United States Patent [19]

Teaney

[11] Patent Number: 5,171,930
[45] Date of Patent: Dec. 15, 1992

[54] ELECTROGLOTTOGRAPH-DRIVEN CONTROLLER FOR A MIDI-COMPATIBLE ELECTRONIC MUSIC SYNTHESIZER DEVICE

[75] Inventor: Dale Teaney, Harrison, N.J.
[73] Assignee: Synchro Voice Inc., Harrison, N.J.
[21] Appl. No.: 589,027
[22] Filed: Sep. 26, 1990
[51] Int. Cl.$^5$ .......................................... G10H 3/12
[52] U.S. Cl. ...................................... 84/725; 381/38; 381/49; 381/151; 381/169; 84/735; 84/743
[58] Field of Search ...................... 381/38, 49, 51-53, 381/151, 169, 170, 187; 84/725, 735, 736, 738, 743, DIG. 9, DIG. 12, 627, 663, 702, 703

[56] References Cited

U.S. PATENT DOCUMENTS

| | | |
|---|---|---|
| Re. 33,739 | 11/1991 | Takashima et al. .............. 84/616 X |
| 3,213,180 | 10/1965 | Cookerly et al. . |
| 3,975,587 | 8/1976 | Dunn et al. . |
| 4,039,754 | 8/1977 | Lokerson . |
| 4,139,738 | 2/1979 | Fourcin . |
| 4,193,332 | 3/1980 | Richardson . |
| 4,202,237 | 5/1980 | Hakansson . |
| 4,319,084 | 3/1982 | Lucchini et al. . |
| 4,459,674 | 7/1984 | Sakurai . |
| 4,463,650 | 8/1984 | Rupert . |
| 4,527,274 | 7/1985 | Gaynor . |
| 4,532,849 | 8/1985 | Drew . |
| 4,627,323 | 12/1986 | Gold ..................................... 84/616 |
| 4,685,448 | 8/1987 | Shames et al. .................. 381/151 X |
| 4,703,505 | 10/1987 | Seiler et al. . |
| 4,709,340 | 11/1987 | Capizzi et al. . |
| 4,757,737 | 7/1988 | Conti ..................................... 84/681 |
| 4,771,671 | 9/1988 | Hoff, Jr. . |
| 4,829,573 | 5/1989 | Gagnon et al. . |
| 4,841,575 | 6/1989 | Welsh et al. . |
| 4,862,504 | 8/1989 | Nomura . |
| 4,885,790 | 12/1989 | McAulay et al. . |
| 4,895,519 | 1/1990 | Beller et al. . |
| 4,905,285 | 2/1990 | Allen et al. . |
| 4,909,118 | 3/1990 | Stevenson . |
| 4,932,303 | 7/1990 | Kimpara ............................. 84/621 |
| 4,982,433 | 1/1991 | Yojima et al. ........................ 381/49 |

OTHER PUBLICATIONS

"Modern Communication Circuits", McGraw-Hill Inc, Co 1986 Author Jack Smith, Editors Rao and Damstra, pp. 188, 189, 481, 482.
Teaney, Fabre-Wheatstone Electroglottograph-A precision R-F Plethysmograph, Ninth Annual Conferenece of the IEEE Engineering in Medicine and Biology Society, Nov. 13-16, 1987.
Teaney, Quantative Electroglottograph—Signal Processing Methods for Clinical Instrumentation, Proceedings of the Annual Internal Conference of the IEEE Engineering in Medicine and Biology Society, Nov. 4-7, 1988.
Glottal Enterprises SC-1 Electroglottograph.
Rothenberg, A Multichannel Electroglottograph, Accepted for publication in the Journal of Voice, May 8, 1991.
"Pitch to MIDI Converters Digigram Midimic & Vicknair Chromatic Translator Module", Keyboard Magazine, Keyboard Report, Dec. 1988.
Product Preview of "voicetracker" by Fairlight Instruments, Pty. Ltd., 1986.
SynchroVoice Research Electroglottograph Brochure, 1982.
Kay Elemetrics Corp. Laryngograph Brochure, Oct. 1986.
Glottal Enterprises SC-1 Electroglottograph Brochure and Price List, Jun. 1991.
Ainsworth, Mechanisms of Speech Recognition, Pergamon 1976, pp. 34-35.

Primary Examiner—William M. Shoop, Jr.
Assistant Examiner—Brian Sircus
Attorney, Agent, or Firm—Darby & Darby

[57] ABSTRACT

A voice-controlled musical device is driven by an electroglottograph as an input to a controller. The electroglottograph (EGG) has a transducer in the form of a band that is located about the user's neck. The EGG converts the cycle of opening and closing of the vocal folds of the user's vocal chords into a clean electrical signal that is particularly accurate with respect to pitch. An output from a microphone integral to the band picks up acoustic dilations of the throat wall concurrent with the glottal cycle and this output is also applied to the controller to indicated vocal source volume. The EGG and microphone signals are combined and converted into a MIDI digital code which can be used to drive a musical synthesizer or a computer. An external switch may be used to alter the attack of a continuous voice performance.

34 Claims, 4 Drawing Sheets

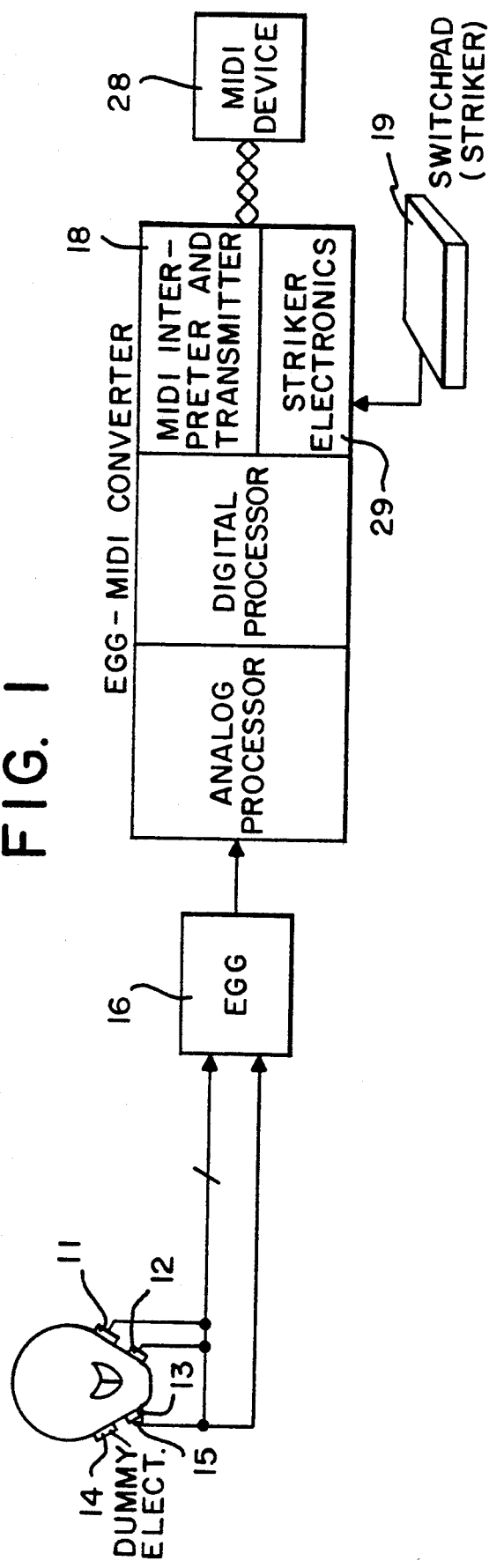
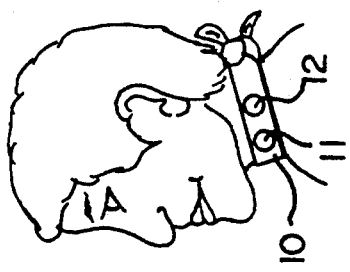
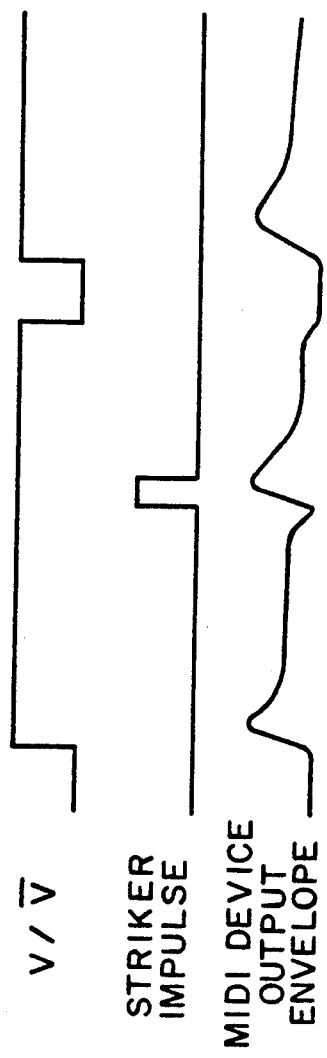

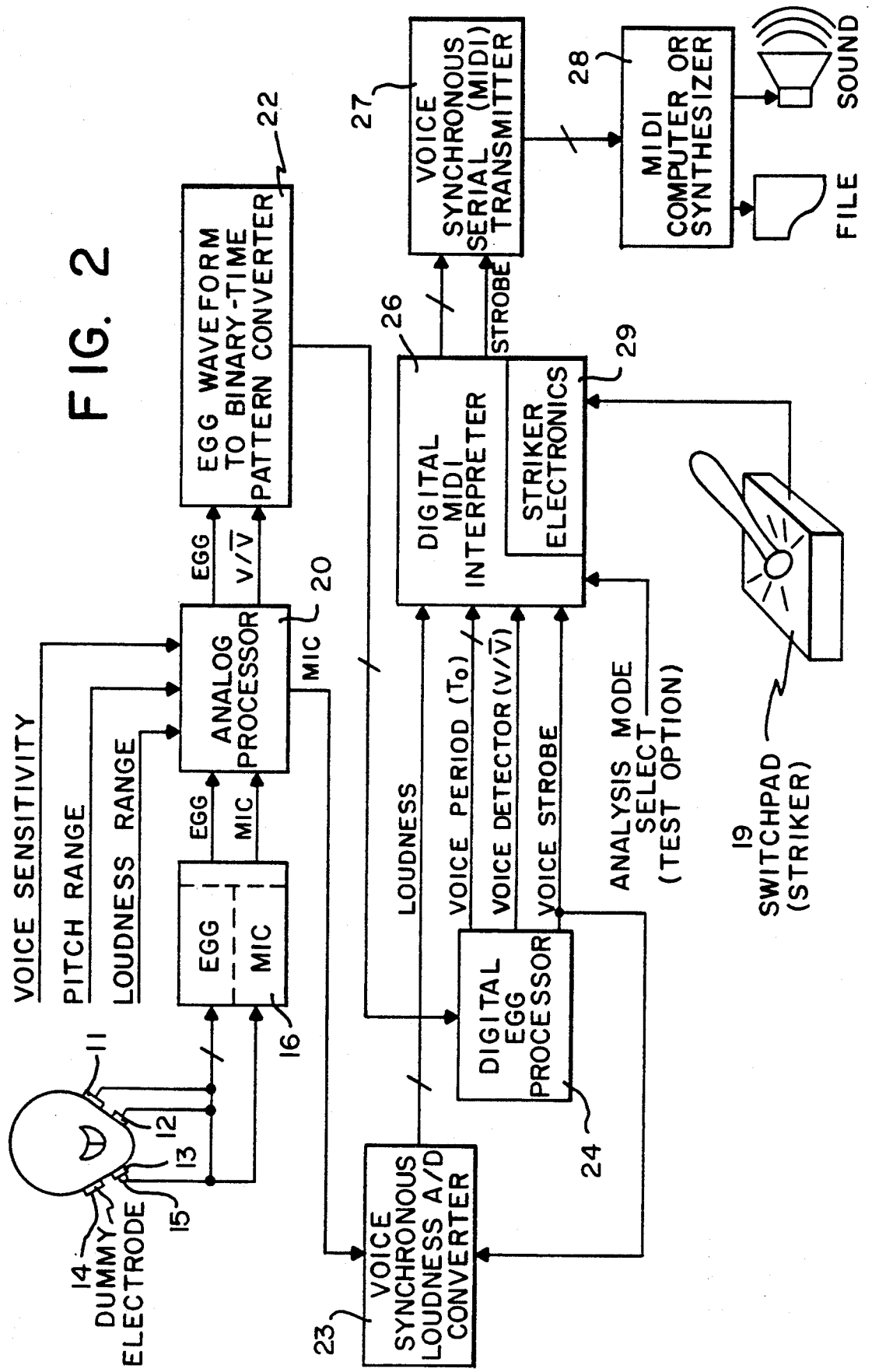

ELECTROGLOTTOGRAPH-DRIVEN CONTROLLER FOR A MIDI-COMPATIBLE ELECTRONIC MUSIC SYNTHESIZER DEVICE

TECHNICAL FIELD

The present invention relates to a voice-controlled electronic music synthesizer device and, more particularly, to an electroglottograph-driven controller for a MIDI-compatible electronic musical device.

BACKGROUND OF THE INVENTION

An electroglottograph (EGG) is a known biosensor having electrodes which contact the subject's neck. The EGG supplies a constant rms current to the neck, e.g. 5 mA, at a frequency of about 5 MHz. When the subject speaks or sings there is a corresponding change in the impedance of the neck at the frequency of the sound being uttered, which change is detected by the electrode as a change in voltage. The EGG, using, e.g., a Wheatstone or Fabre bridge circuit, detects and measures this change in impedance in relation to the frequency of the speech. The EGG provides an accurate waveform of the subject's voice through a full range of frequencies.

The output from a microphone which picks up the sound concurrent with the same vibrations as sensed by the the electrodes may also be applied to the EGG to indicate changes in volume. The EGG has been used for medical diagnosis and speech therapy purposes only. A known EGG device is described in U.S. Pat. No. 4,139,732 to Fourcin, the contents of which are incorporated herein by reference.

Voice-activated musical synthesizers are also known in the art. U.S. Pat. No. 4,771,671 to Hoff and U.S. Pat. No. 4,463,650 to Rupert disclose voice controlled musical devices which use a microphone as an input. U.S. Pat. No. 4,193,332 to Richardson discloses a music synthesizer which receives an input from an instrument or a transducer. Fairlight Instruments Pty. Ltd. of Australia makes and sells "The Voicetracer" which provides real-time synthesizer response to a signal from a microphone.

These prior art devices have not worked well because of the well known difficulties in extracting pitch information from microphone input. Even with cost and time prohibitive amounts of computer processing, pitch extractions are not reliable over a wide range of voicing behaviors and especially in the vicinity of voice onset or release. The physical reasons are 1) the vocal tract filters the glottal source in complex ways that depend on vowel choice, 2) the vocal tract is often configured as a bandpass filter at a frequency above the fundamental, 3) the mouth differentiates the output of the vocal tract, thus further supressing low frequency information, 4) often, especially at voice onset and release, spectral considerations implied by comments 1-3 are irrelevant, and a pulse-by-pulse model is necessary, and 5) the energy from the mouth varies with vowel, microphone position, emphatic segmentation, etc., and furthermore, it is easlily contaminated by ambient sound, the most serious contamination being the matched sound of the synthesizer under control. For these and many other reasons, pitch extraction from a microphone is only marginally useful and has generally failed to meet the extremely demanding requirements of a musical device.

SUMMARY OF THE INVENTION

The present invention is directed to an EGG-driven controller for a MIDI-compatible electronic music synthesizer or like device.

In an illustrative embodiment of the invention a specially designed neckband is placed about the user's neck. This neckband has three active electrodes and may also include a microphone. In the neckband, a fourth inactive, or "dummy", electrode is incorporated to provide physical balance.

The neckband with its electrodes acts as an EGG biosensor and provides an input signal to a signal processor that converts the cycle of opening and closing of the vocal folds into a clean electrical signal that is particularly accurate with respect to pitch. The microphone picks up acoustic dilations of the throat wall concurrent with the glottal cycle and indicates volume. Thus the present invention changes minute voice pitch, loudness and timbre data from the electrodes and microphone into a sequence of real-time serial control words, preferably according to the MIDI protocol (Musical Instrument Digital Interface) for (i) a synthesizer, (ii) a computer program which stores, transforms, or replays the voice pattern, or (iii) another computer program which might, for example, transform the performer's MIDI sequence into traditional music notation. MIDI is widely recognized by computers, electronic music synthesizers and sequencers, and a host of other MIDI-compatible devices.

The invention converts the analog EGG/microphone signals into the digital MIDI control sequence virtually simultaneously with the performer's voice. As a result, the synthesizer output tracks the voice so quickly that the synthesizer literally "sings" with the singer in the synthesized "voice".

Electronic conversion of the performer's laryngeal behavior into a MIDI output is accomplished by a four step process. First, the EGG biosensor detects the length of time (or period) it takes for the performer's larynx to complete one cycle (glottal cycle) by measuring the change in resistance of the performer's throat, and the microphone detects changes in volume. Second, an analog processor of wide dynamic range normalizes the amplitude of the EGG signal and presents it to an analog-to-digital converter. Third, a digital filter and analyzer in the EGG channel make a cycle-by-cycle measurement of voice and vocal source timbre and generate a glottal synchronous strobe for instrument timing purposes. Fourth, the binary data from the digital analyzer is translated into MIDI-intelligible control words by a MIDI interpreter and transmitter which also transmits them to an external MIDI device.

The sequence of MIDI instructions is transmitted at the standard MIDI rate. The formatting and commencement of the first MIDI word transmission requires only about 20 microseconds, so the MIDI command is virtually simultaneous with the completion of the first voice cycle. The MIDI command is sent before the glottal pulse reaches the front of the mouth.

The operation of the present invention is fully automatic. The user selects one of two functions. The first is a test function in which a predetermined series of MIDI instructions is sent to the MIDI instrument to verify that the instrument is operating properly. The other function is the mode selection in which the user selects the pitch and loudness analysis choices. The user may select a continuous pitch, which provides microtonal outputs, or a 12-tone chromatic pitch, which limits the output to the notes of a chromatic scale. The loudness choices are a continuous or variable loudness, which provide either a volume output according the user's vocal volume as detected by the glottal microphone or a fixed loudness level. Selecting continuous pitch and loudness provides full voice tracking, i.e., the synthesizer will exactly mimic the user's voice. Further, the voice range may be set for high (soprano—220 Hz to 1050 Hz), or low (alto and bass—65 Hz to 500 Hz), commonly known as upper and lower voice registers. All of these adjustments are optional refinements of the instrument performance.

In addition to pitch and volume, data on vocal timbre can be extracted from the biosensor by analyzing the velocity of closure and the closure quotient of the EGG waveform, and by spectral analysis of the concurrent glottal microphone signal, especially during the closed phase of the glottal cycle. This timbral information is optionally relayed to the MIDI device as "after touch" data.

Another optional feature of the invention is an external switch which enables the user to superimpose attack characteristics on a continuous or legato vocal performance. By striking a switch pad with a hand, foot, drumstick or the like, a continuous vocal input is given a rhythmic articulation. Although the volume and pitch are controlled by the voice, the attack of the note is controlled by the striker pad. This permits the MIDI output to have attack characteristics which would be impossible for even a highly trained singer to achieve. For example, a synthesizer driven by the present invention may be used to emulate a trumpet, e.g., the singer can use the striker invention to superimpose "triple tongue" effects on the voice signal. Triple tongue is a rapid attack technique which is difficult for a trumpet player to achieve and impossible for a singer to imitate with his larznx. This difficult effect is easily performed by tapping the switch pad.

BRIEF DESCRIPTION OF THE DRAWINGS

The foregoing features of the present invention will be more readily apparent from the following detailed description and drawings of an illustrative embodiment of the invention in which:

FIG. 1 is an overall schematic block diagram of the present invention;

FIG. 2 is a detailed block diagram of an electroglottograph according to the present invention;

FIG. 7 shows the striker pad waveform; and

FIG. 8 is a perspective view of the strap-on biosensor.

DETAILED DESCRIPTION OF THE PREFERRED EMBODIMENTS

Figure 3:
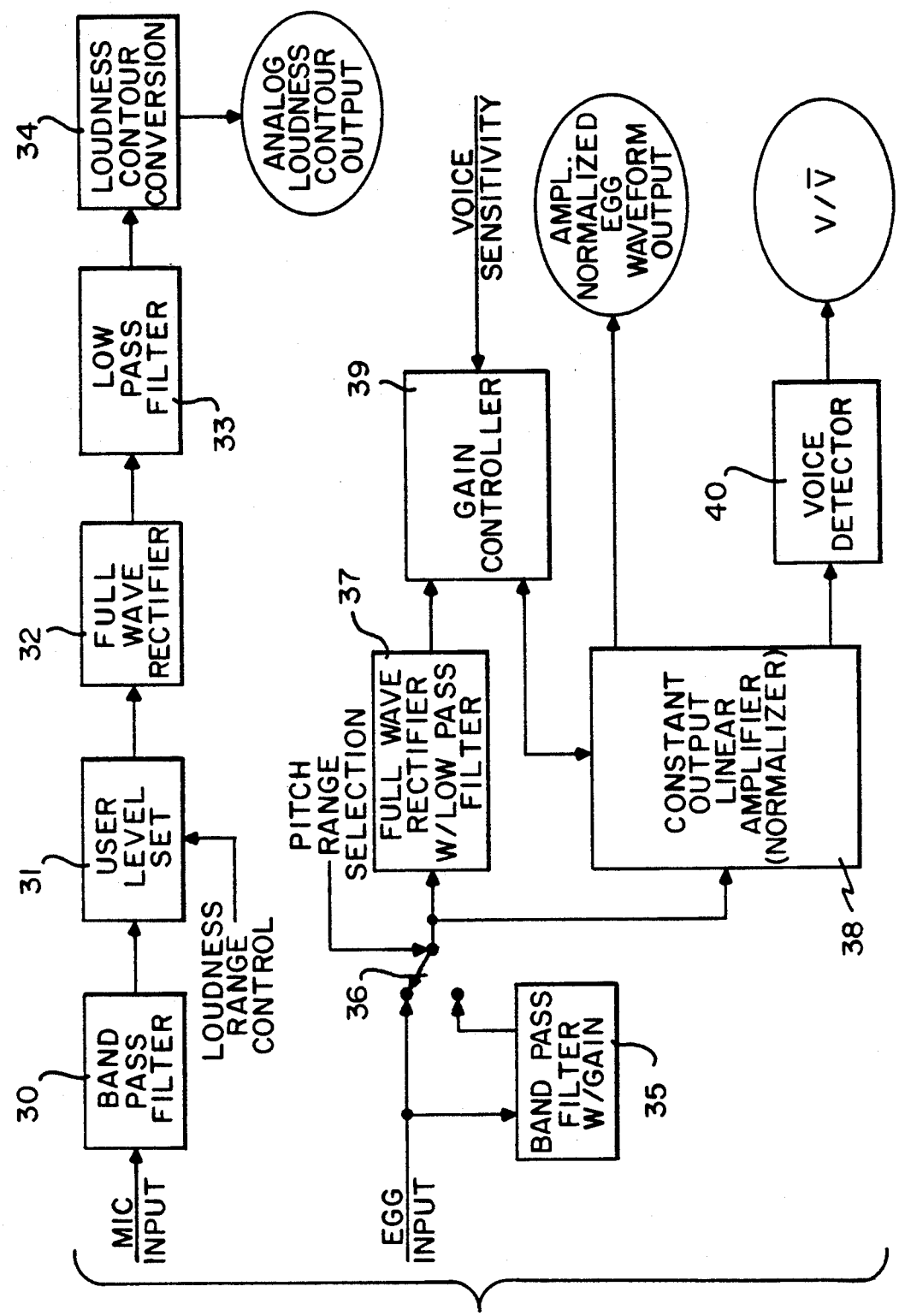
FIG. 3 is a detailed schematic block diagram of the analog processor of the present invention.

FIG. 1 is a simplified block diagram of the present invention. The electroglottograph ("EGG") electrodes 11-14 of a biological sensor of laryngeal function ("biosensor") are attached to the performer's neck. The neckband 10 is a strap-on band made of a soft, pliable substance, preferably polyurethane foam (FIG. 8). The polyurethane foam is held tightly against itself when tied in a half knot as shown. This allows the band to contact the neck without being tight or restricting against the neck.

In order to operate, the band 10 must have three electrodes, one electrode 12, 13 on each side of the thyroid cartilage (the "Adam's apple") and one electrode 11 on the side of the neck. The neck band, according to the present invention, includes a fourth electrode 14, which is a "dummy" electrode located on the opposite side of the neck from the third electrode 11. This dummy electrode 14 serves two related purposes. First, it provides intuitive balance to the user. The user's tendency would be to locate the three electrode arrangement symmetrically with the middle electrode on the center of the neck. However, the EGG will not work in this location. The fourth electrode provides a symmetrical arrangement which feels more natural to the user. Second, the fourth electrode provides a mechanical or physical balance. The dummy electrode evens the stress on each side of the neck and prevents the band from moving once it is strapped on.

The neckband also has an integrally attached microphone 15. For maximum response to vibration of the throat wall, the microphone 15 is integrally attached with an electrode located at the thyroid cartilage, e.g., electrode 13. This also minimizes response to ambient sound (including mouth sound) and simplifies use.

The signals from the biosensor electrodes and microphone are directed to the EGG 16 which translates the change in impedance and volume into an analog signal. The glottal cycle (or period) is extracted from the EGG by detecting the end of each cycle and measuring the time between successive cycles. The general design of the EGG is described in an article by the applicant in the November 1989 Proceedings of the IEEE Conference on Engineering in Medicine and Biology, entitled "Fabre-Wheatstone Electroglottograph—A Precision RF Plethysmograph". The article is incorporated herein by reference.

In general terms the EGG circuit 16 contains transmitter and receiver sections. The transmittor includes an oscillator operating at, e.g., 5 MHz. The output of the oscillator creates a 5 mA current flowing between the electrodes placed on the neck. During phonation the current signal is modulated. This modulation is detected by a balanced bridge which includes the electrodes, 11, 12, 13, and the neck impedance. Also, a feedback control is used in the transmitter section to stabilize the current at 5 mA rms. Thus, the EGG circuit 16 creates a measurement current and detects the change in the current due to phonation.

The analog signals from the EGG are applied to the EGG-MIDI converter 18. The EGG-MIDI converter 18 is comprised of an analog processor, a digital processor, and a MIDI interpreter and transmitter. The EGG-MIDI converter changes the analog signals from the EGG into a MIDI control signal, which in turn is applied to a MIDI device 28. The MIDI device may be a computer which makes later use of the signal, or a synthesizer or sequencer which immediately produces music in response to the signal. The MIDI signal may be altered further by a switch pad 19, as described below.

FIG. 2 is a more detailed block diagram of the EGG-driven controller for the MIDI-compatible electronic music device shown in FIG. 1.

The output of the electrodes 11-13 and the microphone 15 are separately received in the receiver section of the EGG circuit 16. The receiver separately provides the EGG signal and the microphone signal to the analog processor 20, where the EGG signal is amplitude normalized and the microphone output is converted into a loudness contour signal. Also, the voice sensitivity, pitch range selection and loudness sensitivity may be input to the processor 20.

The output of the analog processor 20 is an amplitude normalized EGG signal which is applied to an EGG waveform to binary-time pattern converter 22 that provides three output signals that indicate the relationship of the EGG signal to plus and minus threshold levels and zero crossing. These signals are applied to a digital EGG processor 24. The digital EGG processor 24 compares the three level binary signals to a time reference and creates three other signals, i.e., the voice period ($T_0$), the voice detector (V/$\overline{V}$) and the voice strobe (strobe).

The microphone signal, after being converted to a loudness contour signal by the analog processor 20 is directed to a voice-synchronous loudness analog-to-digital converter 23. The voice-synchronous loudness A/D converter 23 creates digital signals which represent loudness.

The outputs of converter 23 and processor 24 are received by the digital MIDI interpreter 26 which interprets this information to create MIDI-intelligible signals. The interpreter 26 also receives the analysis mode selection signal, which allows the user to select either the test option or the input option and to select the mode of voice tracking. The interpreter 26 prepares the MIDI signal for the voice synchronous serial (MIDI) transmitter 27 that provides the MIDI signal to a MIDI computer or synthesizer (MIDI instrument) 28. The MIDI interpreter 26 may also receive an attack input from an external switch pad 19, as described below. The MIDI instrument either stores the information or uses the information to create sound, e.g., music.

FIG. 3 shows a schematic diagram of the analog processor 20 of the EGG-MIDI converter. The analog processor 20 separately treats the microphone and EGG signals. The microphone signal is received by the analog processor and passed through a band pass filter 30 which eliminates unwanted frequencies. The user can operate the loudness control by setting the level in the same way that the VU meter is adjusted on a tape recorder. Next, the filtered microphone signal is full wave rectified in rectifier 32. The rectified signal is then passed through a fast-rise, slow-release low pass filter 33. The loudness contour converter 34 changes the linear amplitude envelope to a non-linear envelope corresponding to the somewhat logarithmic volume scale typical of MIDI devices. This analog signal is then directed to the digital MIDI interpreter 26, discussed below.

The EGG signal is converted in the analog processor 20 to a constant amplitude. The user sets the voice sensitivity by choosing the lowest signal that will be amplified to the constant output level. The amplifier controller 39 responds to the incoming EGG signal. The EGG signal is selectively passed through a band pass filter 35 with gain, depending on the pitch range selected by the user by operating switch 36. The range selection adapts the modal change in the EGG between high voice, i.e., upper register, and lower voice. The EGG signal is then passed from the pitch range switch 36 to a constant output linear amplifier (normalizer) 38. The EGG signal is also applied to a full wave rectifier and low pass filter 37. The output of the full wave rectifier and low pass filter is directed to a user controlled gain controller 39. The user control is a voice sensitivity adjustment which provides for the ambient electronic noise conditions, not for intramodal EGG amplitude changes. The output of gain controller 39 is sent to the constant output linear amplifier (normalizer) 38 to control its gain and normalize its output. The output of the normalizer 38 is the amplitude normalized EGG waveform output. The normalizer 38 output is also applied to the voice detector 40, which analyzes the EGG signal and determines whether the signal represents a valid glottal cycle, as will be explained further below.

Figure 4:
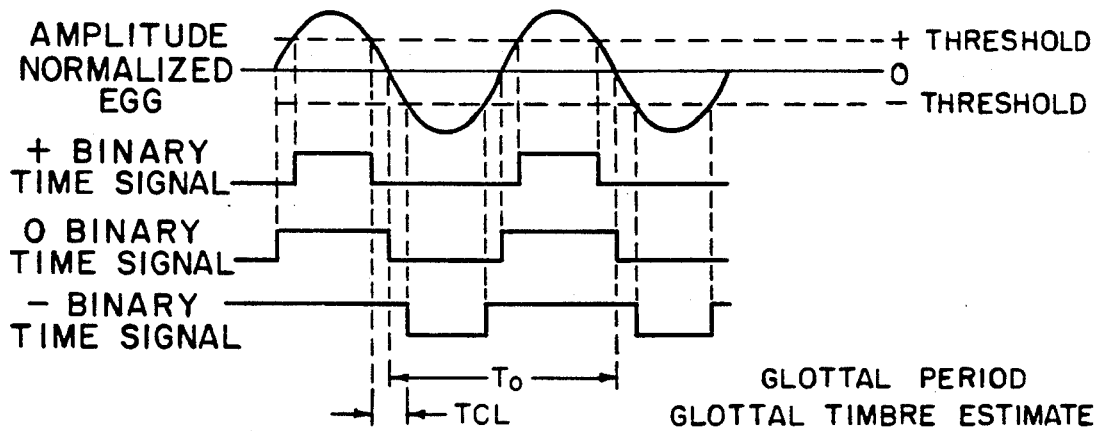
FIG. 4 shows the waveforms for the analog-to-binary time pattern conversion.

FIG. 4 shows the waveforms of the normalized EGG signal and the three binary-time signals produced in the EGG-waveform-to-binary-time pattern converter 22. In converter 22 the amplitude of the amplitude normalized EGG signal is compared to a positive and a negative threshold. Three binary-time signals are produced by this comparison. The first signal is the "positive signal." When the EGG amplitude exceeds the positive threshold a "1" digital signal is generated. When the amplitude falls below this threshold the "positive signal" returns to a "0" digital signal. When the amplitude drops below the negative threshold a "0" digital signal is generated for the second signal, the "negative signal". It returns to a "1" digital signal when the amplitude rises past this threshold. The third signal, the "zero signal", reads a digital "1" when the EGG signal rises through the zero amplitude line, and switches to a "0" digital signal when the EGG signal drops across the zero amplitude line. The time between the negative edges of the "zero signals" is the glottal cycle or period ($T_0$) and the time between the positive and negative threshold is the glottal timbre estimate (TCL).

Figure 5:
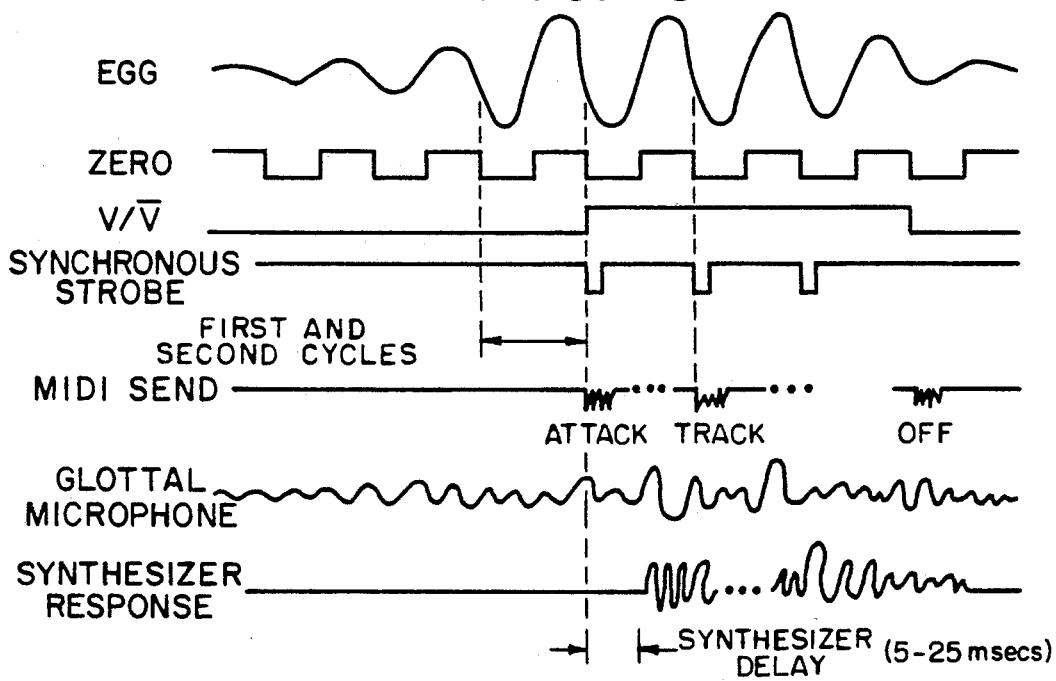
FIG. 5 shows the waveforms for the EGG-to-MIDI output conversion.

FIG. 5 shows the waveforms for the EGG-processing-to-MIDI output. The digital EGG processor 24 uses the three binary-time signals described above as emanating from the converter 22 in order to determine valid voicing and to measure the pitch period for the glottal cycles. The diagram shows the normalized EGG signal from analog processor 20, the binary-time "zero signal" from converter 22 and a voice detector signal (V/$\overline{V}$).

V/$\overline{V}$ indicates that the first valid glottal cycle has been completed. The voice detector signal (V/$\overline{V}$) is generated by the voice detector 40, as shown in FIG 3. The voice detector 40 analyzes the configuration of the amplitude normalized EGG waveform to determine whether or not the waveform corresponds to the configuration of a valid glottal cycle by comparing the waveform to known glottal cycle waveforms. When a complete valid glottal cycle is detected, the voice detector signal (V/$\overline{V}$) reads a digital "1". When no valid glottal cycle is detected, the voice detector signal (V/$\overline{V}$) reads a digital "0". The voice detector 40 is particularly effective in discriminating unwanted signals, such as ambiant noise or interference, from the desired signal.

Once the first valid cycle has been detected, a strobe signal is created which locates in real-time the last complete glottal cycle. The glottal cycle measurements are made by linear binary counts of a known frequency reference. The MIDI signal is transmitted when the V/$\overline{V}$ signal is on. The MIDI message corresponding to the vocal attack is initiated within a few microseconds of the voicing determination. The synthesizer response is based on the information from the EGG and microphone outputs. This response experiences a slight delay caused by the time necessary for the synthesizer to respond to the MIDI information. This delay is on the order of one glottal cycle.

Figure 6:
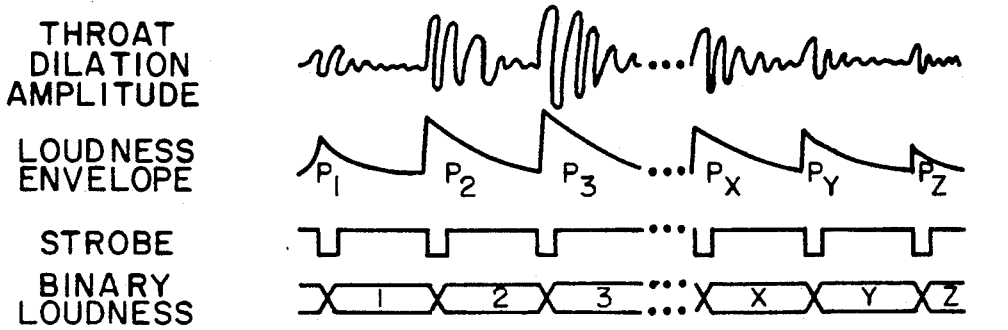
FIG. 6 shows the loudness waveforms.

FIG. 6 shows the waveforms involved in the voice synchronous loudness analog-to-digital converter 23. The loudness digitizer samples the loudness contour at the same phase point in each glottal cycle, a point which follows glottal closure. This allows the digital sequence to be smooth and to change rapidly from cycle to cycle to track vocal gesture. The throat dilation amplitude creates a loudness envelope which outlines the dilation amplitude. The strobe indicates the sampling of the loudness A/D converter. The sampling results in a binary loudness signal.

The binary representations of the pitch period (EGG) and loudness (microphone) signals are presented to the processor for each glottal cycle. The user chooses a suitable musical representation of the vocal source for the intended purpose:
Pitch: Continuous or 12 tone
Loudness: Continuous or fixed.

The present invention may also include various options such as timbrel aftertouch, transpositions and the like. The MIDI interpreter 26 translates the binary data into a stack of MIDI instructions according to the choices set out above and the standard MIDI-control language. The formatting process performed by interpreter 26 also handles the highly-disparate data rates. Detailed voice tracking involves several binary words per glottal cycle, and voice frequencies from 66 to 1100 Hz require data rates which are far in excess of the synthesizer's ability to respond. The formatter samples the voice data, and, in turn, updates the synthesizer's instructions at an appropriate rate, which is about 50 Hz.

MIDI instruments, e.g., synthesizers, computers and sequencers, are highly variable devices; so it is necessary to provide a test protocol. The test protocol option is selected by the user and it transmits a set MIDI instruction which tests the receiving device's response to key, bend, velocity, control volume and aftertouch. The user can be sure from the test that the MIDI instrument will respond properly to the MIDI instructions from the device.

The MIDI transmitter 27 (FIG. 2) sends out to the MIDI instrument 28 a serial sequence or stack of MIDI control words prepared by the interpreter 26. A feature of the present invention is that the transmission of the MIDI message is sent synchronously with the glottal cycle. This is important because the biosensor is a highly sensitive electronic device which is unavoidably interfered with by bursts of electromagnetic interference such as, for example, the MIDI transmission itself. By synchronizing the MIDI burst with the glottal cycle, the unavoidable interference is rendered harmless to the precise measurements necessary for satisfactory continuous voice tracking. The EGG measures the length of the glottal period, so relevant information is detected at the end of each period. This information is transformed into a MIDI instruction and transmitted within a few microseconds, long before the next glottal cycle is complete. Because the MIDI instruction is transmitted during the glottal cycle (when the EGG is insensitive to interference) and not at the end of it (when the EGG is subject to interference), it does not interfere with the EGG's measurements.

FIGS. 1 and 2 show an external switch pad 19, which is part of the optional striker feature. A known external switch pad is used to generate a digital electronic signal when it is struck by a hand, foot, drumstick or the like. The digital signal is created by a known switch-to-pulse converter. This electronic signal is transmitted to the striker electronics 29 which is part of the MIDI Interpreter 26. The striker electronics comprise a known debounce circuit. The debounce circuit relays a clean strike pulse signal to the MIDI interpreter which recognizes the pulse as an attack message. The pitch and energy (a parameter known in MIDI as "velocity") of the new attack are determined by the ongoing voice input.

FIG. 7 shows a timing diagram for the striker feature. The voice detector signal V/$\overline{V}$ indicates two blocks of constant voicing separated by a typical voice interruption, i.e., a brief interval of silence. The strike impulse diagram shows a pulse sent to the MIDI interpreter in response to striking the switch pad. The resultant MIDI device output envelope shows a new note attack signal is output, even though the vocal input is continuous.

This striker feature allows the user to superimpose rapid or complex emphatic and percussive musical effects onto a continuous vocal input. Effects which may be impossible to be achieved even by the most highly trained singer can be easily performed using the striker option.

While the invention has been particularly shown and described with reference to preferred embodiments thereof, it will be understood by those skilled in the art that various changes in form and details may be made therein without departing from the spirit and scope of the invention.

What is claimed is:

1. An apparatus comprising:
   an electroglottograph which produces a signal containing a pitch information in response to a movement cycle of a user's vocal cords;
   means for converting the electroglottograph signal into a digital electronic musical signal; and
   means for transmitting the digital electronic music signal to a compatible music generating real time serial digital interface.

2. The apparatus of claim 1, wherein the electroglottograph includes a neckband having four symmetrically arranged electrodes, which, when in place, locates first and second ones of said electrodes along each side of the user's thyroid cartilage, third one of said electrodes on one side of the user's neck and fourth inactive one of said electrodes on the other side of the neck opposite the third electrode.

3. The apparatus of claim 1, wherein the electroglottograph also includes a microphone for detecting an amplitude of sounds resulting from movement of the user's vocal cords.

4. The apparatus of claim 3, wherein the converting means comprises an analog signal processor, ana analog-to-digital converter and a computer code interpreter.

5. The apparatus of claim 1, wherein the digital interface is a Musical Instrument Digital Interface (MIDI) device.

6. The apparatus of claims 4 and 33, wherein the analog processor comprises a microphone output signal processor for receiving the volume signal and an electroglottograph output signal processor.

7. The apparatus of claim 6, wherein the microphone output signal processor includes, in series, a band pass filter, a full wave rectifier, a low pass filter and a loudness contour converter.

8. The apparatus of claim 7, wherein the microphone output signal processor further includes an electronic user controlled loudness control.

9. The apparatus of claim 6, wherein the electroglottograph output signal processor includes a constant output linear amplifier with an amplifier input and a feedback input, said electroglottograph signal being applied to the amplifier input and to a full wave rectifier with a low pass filter, the output of the low pass filter being applied to a gain controller connected in series with it and the output of the gain controller being applied to the feedback input.

10. The apparatus of claim 9, wherein the electroglottograph output signal processor further includes:
   a user selectable band pass filter with gain, which output is received by the full wave rectifier and the amplifier input of said constant output linear amplifier; and
   a switch means for selectively by-passing the band pass filter or passing the electroglottograph signal through it.

11. The apparatus of claim 9, wherein the electroglottograph output signal processor further includes a user operated voice sensitivity control which varies the gain output of the gain controller.

12. The apparatus of claim 4, wherein the digital processor comprises:
   an electroglottograph waveform-to-binary-time pattern converter for converting the electroglottograph signal into binary signals indicating the timing of the electroglottograph signal;
   a digital electroglottograph processor which generates a voice period signal, a voice detection signal and a strobe signal; and
   a voice synchronous loudness analog-to-digital converter for converting a microphone signal into a digital loudness signal.

13. The apparatus of claim 4, wherein the computer code interpreter comprises a digital MIDI formatting circuit.

14. The apparatus of claim 4, wherein the computer code interpreter includes a user operated mode selection means for enabling the user to choose between generating a converted electroglottograph signal and a test signal, the test signal replacing a MIDI control sequence.

15. The apparatus of claim 4, wherein the computer code interpreter receives an externally generated new note attack signal for superimposing attack characteristics over a continuous voice signal.

16. The apparatus of claim 15, wherein the externally generated attack signal is generated by a switch.

17. The apparatus of claim 1, wherein the transmitting means is a voice synchronous serial transmitter.

18. The apparatus of claim 1, wherein the electronic signal transmission is synchronized to occur during the vocal chord cycle.

19. An apparatus comprising:
   an electroglottograph EGG means for producing an electroglottograph signal containing pitch information generated in response to a movement cycle of a user's vocal cords to produce sound;
   a microphone for generating a microphone signal indicative of the volume of the sound;
   means for combining the EGG and microphone signals and converting the combined signal into a Music Instrument Digital Interface (MIDI) signal, the converting means including an analog signal processor for normalizing the electroglottograph signal, an analog-to-digital processor for converting the normalized electroglottograph signal into a digital signal, a MIDI interpreter for translating the digital signal into a MIDI format signal; and
   a voice synchronous serial transmitter for transmitting the MIDI signal to a MIDI device.

20. The apparatus of claim 19, further comprising an external switch which generates a digital signal, said digital signal being translated by the MIDI translator as a new note attack.

21. A method for controlling a digital musical instrument with an electroglottograph signal, said signal being generated at the end of a user's glottal cycle, comprising the steps of:
   generating an electroglottograph signal;
   amplitude normalizing the electroglottograph signal;
   digitizing the normalized signal;
   formatting the digitized signal into a computer music code; and
   transmitting the formatted signal to a compatible digital music generating real time serial digital interface.

22. The method of claim 21, further including the step of analyzing a volume signal with the electroglottograph signal.

23. The method of claim 21, wherein the step of formatting involves converting the digitized signal into a Musical Instrument Digital Interface (MIDI) computer code.

24. The method of claim 21, wherein the step of amplitude normalizing includes generating an analog loudness contour signal from the microphone signal and an amplitude normalized electroglottograph waveform signal from the EGG signal.

25. The method of claim 21, wherein the step of digitizing includes the step of converting the amplitude normalized electroglottograph signal into a binary-time pattern signal.

26. The method of claim 25, wherein the step of binary-time pattern converting includes the step of forming three binary time signals, one signal indicating when the amplitude exceeds a positive threshold, a second signal indicating when a zero amplitude is crossed and a third signal indicating when the amplitude falls below a negative threshold.

27. The method of claim 21, wherein the step of transmitting occurs synchronously with the user's glottal cycle.

28. The method of claim 21, further comprising the step of generating an attack signal, said attack signal being converted into the computer code.

29. The method of claim 28, wherein the attack signal is generated by striking an external switch.

30. The apparatus of claim 1 further including a device for altering the attack of the digital musical signal, comprising:
   means for generating a digital pulse;
   means for transmitting the digital pulse to the digital interface; and
   menas for translating the digital pulse into a digital attack signal superimposed on the digital musical signal of the digital interface.

31. The apparatus of claim 30, wherein the means for generating includes a switch pad and a switch-to-pulse converter; and the means for transmitting includes a debounce circuit.

32. In an electroglottograph, a neckband composed of a pliable substance which, when in place, contacts a user's neck, characterized in that:

the neck band includes four electrodes for contacting the user's neck;

two of said electrodes are located at either side of the user's thyroid cartilage;

the third of said electrodes is located on one side of the user's neck; and the fourth of said electrodes is inactive and is located on the opposite side of the neck as the third electrode;

wherein said first, second and third electrodes detect electrical changes in the impedance of the user's neck and transmit information on such changes to the electroglottograph.

33. The apparatus of claim 1, further including a microphone for producing a volume signal containing volume information.

34. An electroglottograph-to-Musical Instrument Digital Interface (MIDI) converter, comprising:

input means for receiving an analog electroglottograph signal;

means for converting the electroglottograph signal into a MIDI signal;

means for transmitting the MIDI signal to a compatible MIDI device.

* * * * *